United States Patent
Jung

(10) Patent No.: US 10,898,661 B2
(45) Date of Patent: Jan. 26, 2021

(54) NEBULIZER AND CONTAINER

(71) Applicant: Boehringer Ingelheim International GmbH, Ingelheim am Rhein (DE)

(72) Inventor: Andree Jung, Idar-Oberstein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 710 days.

(21) Appl. No.: 15/345,646

(22) Filed: Nov. 8, 2016

(65) Prior Publication Data
US 2017/0128681 A1    May 11, 2017

(30) Foreign Application Priority Data
Nov. 9, 2015   (EP) .................................... 15020223

(51) Int. Cl.
*A61M 15/00* (2006.01)
*A61M 11/00* (2006.01)
*B05B 11/00* (2006.01)

(52) U.S. Cl.
CPC ...... *A61M 15/0081* (2014.02); *A61M 11/006* (2014.02); *A61M 11/007* (2014.02); *A61M 15/0065* (2013.01); *A61M 15/0068* (2014.02); *A61M 15/0071* (2014.02); *A61M 15/0026* (2014.02); *A61M 2202/0007* (2013.01); *A61M 2202/0468* (2013.01); *A61M 2202/064* (2013.01); *A61M 2205/273* (2013.01); *B05B 11/0054* (2013.01); *B05B 11/3091* (2013.01)

(58) Field of Classification Search
CPC ............ A61M 11/006; A61M 15/0068; A61M 15/0081; A61M 15/0065; A61M 11/007; A61M 15/0071; A61M 15/0026; B05B 11/0054; B05B 11/3091
See application file for complete search history.

(56) References Cited

U.S. PATENT DOCUMENTS

| 5,482,030 | A | 1/1996 | Klein |
| 6,149,054 | A | 11/2000 | Cirrillo et al. |
| 7,823,584 | B2 * | 11/2010 | Geser ............... A61M 15/0065 128/200.17 |
| 2005/0087191 | A1 | 4/2005 | Morton et al. |
| 2012/0080448 | A1 | 4/2012 | Carrico et al. |

(Continued)

FOREIGN PATENT DOCUMENTS

| EP | 2614848 A1 | 7/2013 |
| GB | 1488719 A | 10/1977 |
| JP | 2010011884 A | 1/2010 |

(Continued)

OTHER PUBLICATIONS

Abstract in English for JP2010011884, Jan. 21, 2010.
International Search Report for corresponding application PCT/EP2016/076485, dated Feb. 14, 2017.

*Primary Examiner* — Theodore J Stigell
(74) *Attorney, Agent, or Firm* — Matthew Dernier, Esq.

(57) ABSTRACT

A nebulizer as well as a container with a fluid for such a nebulizer are proposed. The container comprises a control device which indicates initially an unused state of the container before first use. An indicator device stops via a locking device further use of the container in a locked state when a predetermined number of uses has been reached or exceeded. After replacement of the container, the nebulizer can be reset and used again.

25 Claims, 8 Drawing Sheets

(56) References Cited

U.S. PATENT DOCUMENTS

Figure 1:
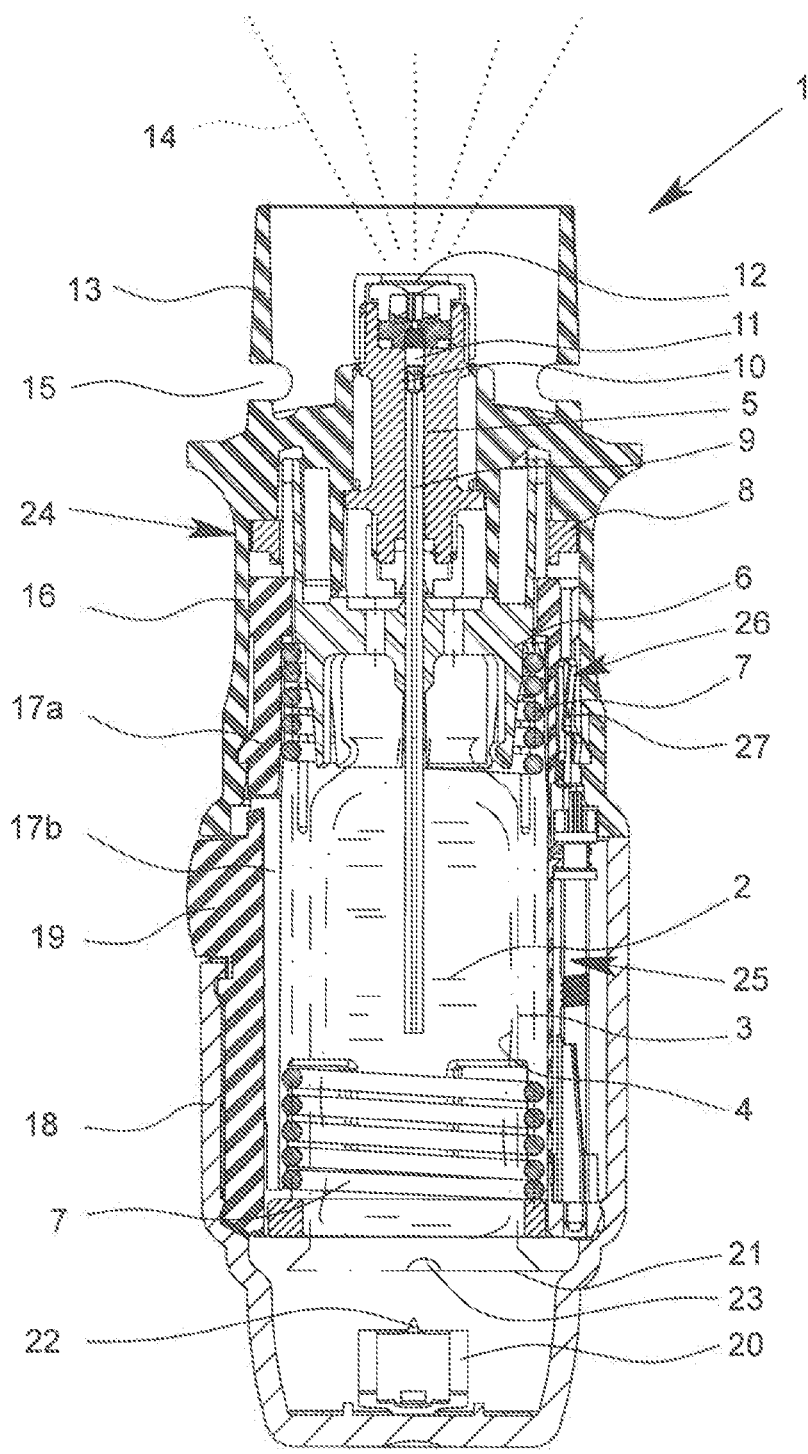

2012/0325204 A1    12/2012   Holakovsky et al.
2013/0125880 A1     5/2013   Holakovsky et al.

FOREIGN PATENT DOCUMENTS

| WO | 1996006011 A2 | 2/1996 |
| WO | 199628205 A1 | 9/1996 |
| WO | 2001003851 A1 | 1/2001 |
| WO | 2005087299 A1 | 9/2005 |
| WO | 2007022898 A2 | 3/2007 |
| WO | 2009115200 A1 | 9/2009 |
| WO | 2012160047 A2 | 11/2012 |
| WO | 2012162305 A1 | 11/2012 |
| WO | 2015149921 A1 | 10/2015 |
| WO | 2015169430 A1 | 11/2015 |
| WO | 2015169732 A1 | 11/2015 |
| WO | 2015169759 A1 | 11/2015 |

* cited by examiner

NEBULIZER AND CONTAINER

The present invention relates to a nebulizer with a replaceable container holding fluid to be nebulized, and means to track use of such containers with the nebulizer.

WO 2012/162305 A1 discloses a nebulizer. A container can be inserted into a housing of the nebulizer. The housing is closed by a lower housing part. By rotating the housing part the drive spring can be put under tension and fluid can be sucked into a compression chamber of the pressure generator. Simultaneously, the container is moved into the lower housing part in a stroke movement within the nebulizer. After manual pressing a button, the drive spring is released and moves a delivery tube into the pressure chamber so that the fluid is put under pressure by the drive spring and is delivered or atomized through a nozzle into a mouthpiece as an aerosol or mist, without the use of propellant gas. Thus, the container is moving axially forth and back during conveying of the fluid to be nebulized, and during pressure generation and nebulization. The nebulizer comprises an indicator device for counting and/or indicating a number of uses performed or still possible. The indicator device blocks further use in a locked state when a predetermined number of uses has been reached or exceeded with the current container. Then, the container can be replaced together with the housing part and the nebulizer can be used further with the new container.

WO 2007/022898 A2 discloses a similar nebulizer, wherein a counter device can be integrated into a housing part that is exchangeable or replaceable together with the container, which is inseparable from the housing part.

Object of the present invention is to provide a nebulizer and a container for a nebulizer allowing easy and/or secure operation and handling and/or a compact and/or reliable construction, preferably while allowing replacement of the container without replacement of any housing part of the nebulizer and preferably preventing reuse or reinsertion of an already used container.

The present invention relates to a nebulizer for nebulizing a fluid, preferably liquid medicament, from a replaceable container containing the fluid, and relates to the container.

The nebulizer comprises a locking device for blocking further use of the nebulizer with the container in a locked state after usual use, in particular after the number of uses of the nebulizer with the container has reached or exceeded a predetermined number of uses, and/or for blocking use of the nebulizer in a delivery state without container.

According to the present invention, the container comprises a control device for indicating initially an unused state of the container and unblocking the nebulizer by unlocking the locking device. This allows a very simple realization and reset of the nebulizer by replacing a used container against an unused container.

According to an alternative or additional aspect of the present invention, the container comprises the control device for indicating a used state of the container to avoid unblocking of the nebulizer or unlocking of the locking device. Thus, reuse or reinsertion of an already used container can be prevented.

Preferably, an indicator device is provided for counting and/or indicating the number of uses already performed or still possible with the container.

Preferably, the nebulizer comprises a housing part which can be opened or detached from the nebulizer for inserting or replacing the container. In particular, the indicator device is arranged in or inseparable from this housing part.

In particular, the indicator device or the associated locking device can block the nebulizer or can cause the blocking of the nebulizer against further use in the locked state when a predetermined number of uses has been reached or exceeded with the respective container.

In particular, the control device is for actuating or resetting the indicator device or locking device of the nebulizer, in particular when the container is used for the first time with the nebulizer.

Preferably, the control device unlocks, actuates or controls the locking device indirectly, in particular via the indicator device.

Preferably, the control device initially resets the indicator device and/or resets the locked state of the nebulizer when an unused container is used for the first time with the nebulizer and/or is inserted for the first time in the nebulizer.

Preferably, the nebulizer 1 is delivered in the locked state without a container 3 being connected or inserted. Thus, the nebulizer 1 is blocked against use in its delivery state, in particular by means of the locking device. This first locked state can be overcome preferably only by connecting or inserting an unused container and, in particular, (completely) closing the nebulizer.

Preferably, the indicator device controls or actuates the locking device.

Preferably, the nebulizer comprises a housing part which can be detached from the nebulizer or opened for replacing the container.

Preferably, the indicator device is arranged in the housing part.

Preferably, the locking device is adapted to block tensioning of the nebulizer in the locked state.

The blocking of the nebulizer against further use can be overcome by replacing the container against one not yet used.

Preferably, the control device is inseparably connected with the container or with a container housing of the container, but separable from the nebulizer or its housing and from the housing part, so that the control device is replaceable together with the container. This allows reuse of the nebulizer and the housing part preferably including the indicator device with another container including another control device. Thus, the overall size of the components to be exchanged is kept small, so that the replacement packages are size reduced, so that transport of a large number of packages is facilitated.

Preferably, the control device is fixedly arranged at a bottom of the container and/or opposite to an outlet of the container. This allows a very compact construction. Further, the control device does not interfere with the fluidic connection of the container to the nebulizer or vice versa.

In particular, the control device comprises a control member which is preferably moveable, in particular depressable and/or axially moveable.

Preferably, the control member is held in different positions before and after first use or insertion into the nebulizer in order to indicate, in particular in a first position, initially an unused state of the associated container, and, in particular in a second position, an already used state of the associated container.

The term "used" or "used state" means with respect to the container in particular that the container has already discharged at least one dose of fluid with the nebulizer, in particular up to the predetermined number of uses, or that the container has been inserted into the nebulizer, in particular with completely closed housing of the nebulizer, or that the container has been (fluidically and/or mechanically) connected with the nebulizer at least once.

The term "unused" or "unused state" means with respect to the container in particular that the container has not been used for discharging at least one dose of fluid and/or that the container has not been inserted into the nebulizer, in particular with completely closed housing of the nebulizer, and/or that the container has not been (fluidically and/or mechanically) connected with the nebulizer at least once.

In addition, the control member may assume an intermediate position or state between the first and second positions. Preferably, the intermediate state may result in that the control device or control member indicates a used state and/or is not suitable for or prevents unblocking of the nebulizer when the respective container is (again) inserted into or connected to the nebulizer. In this intermediate state, the container may be considered as being "used" although any fluid has not been discharged from the container, in particular any tensioning has not taken place with the container.

Preferably, the control device or control member do not unblock the nebulizer or locking device if an already used container is reinserted into or reconnected with the nebulizer, in particular because the control member device or is not in its initial or first position required for unblocking.

Preferably, the locked state is automatically reset by the control device or its control member when the used container is inserted into or connected with the nebulizer, preferably when completely closing the nebulizer.

Preferably, the indicator device is automatically reset when the used container is inserted into or connected with the nebulizer, preferably when completely closing the nebulizer.

Preferably, the indicator device comprises at least one indicator element and an actuation element for indexing the indicator element(s). In particular, the indicator element displays an indication of the number of uses already performed or still possible with the respective container.

Preferably, a linear or axial movement of the actuation element causes a rotational movement of the indicator element.

Even more preferably, the actuation element is set in motion by a relative longitudinal movement between the container with the indicator device and the housing and/or housing part of the nebulizer.

The above aspects of the present invention and the further aspects described below can be realized independently from each other, and in any combination.

Figure 2:
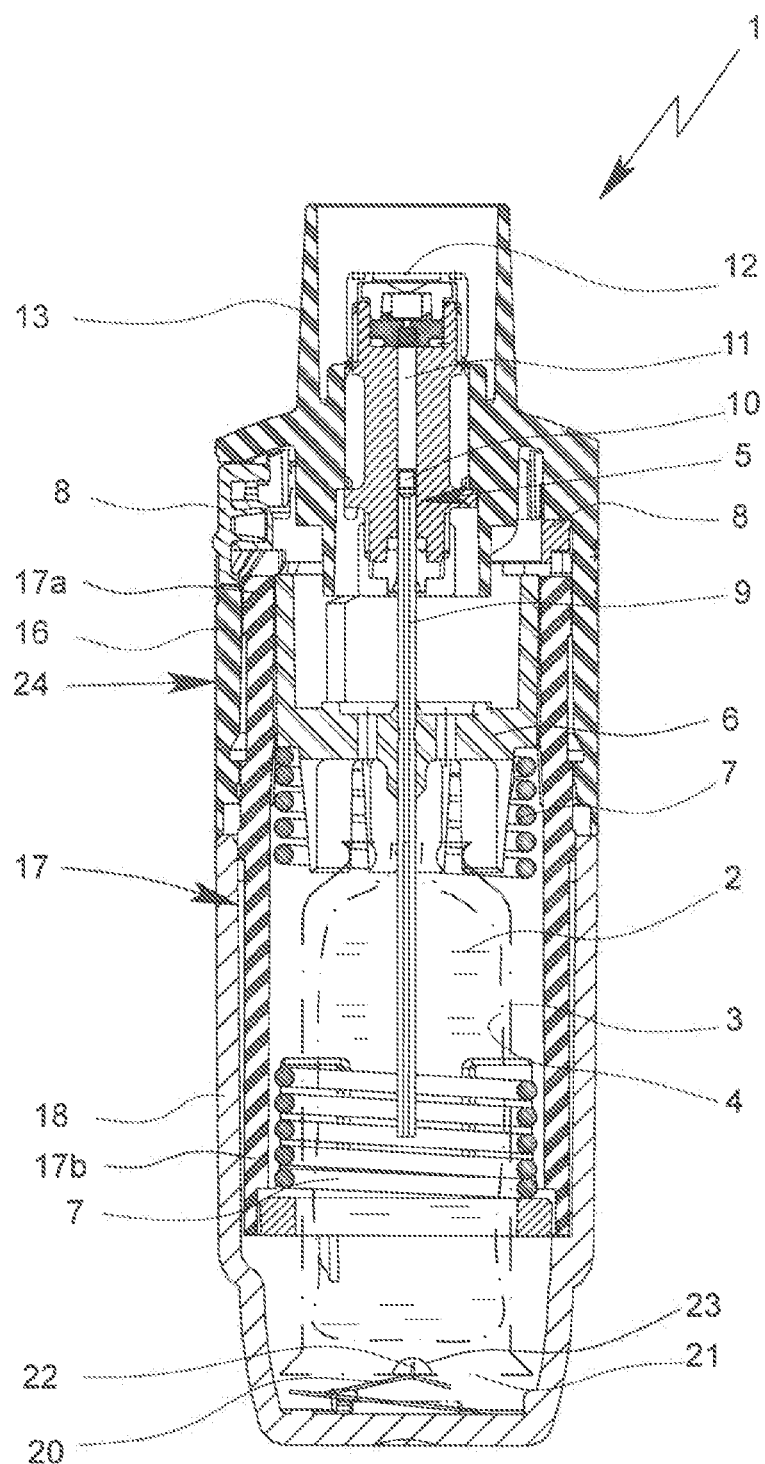
Figure 3:
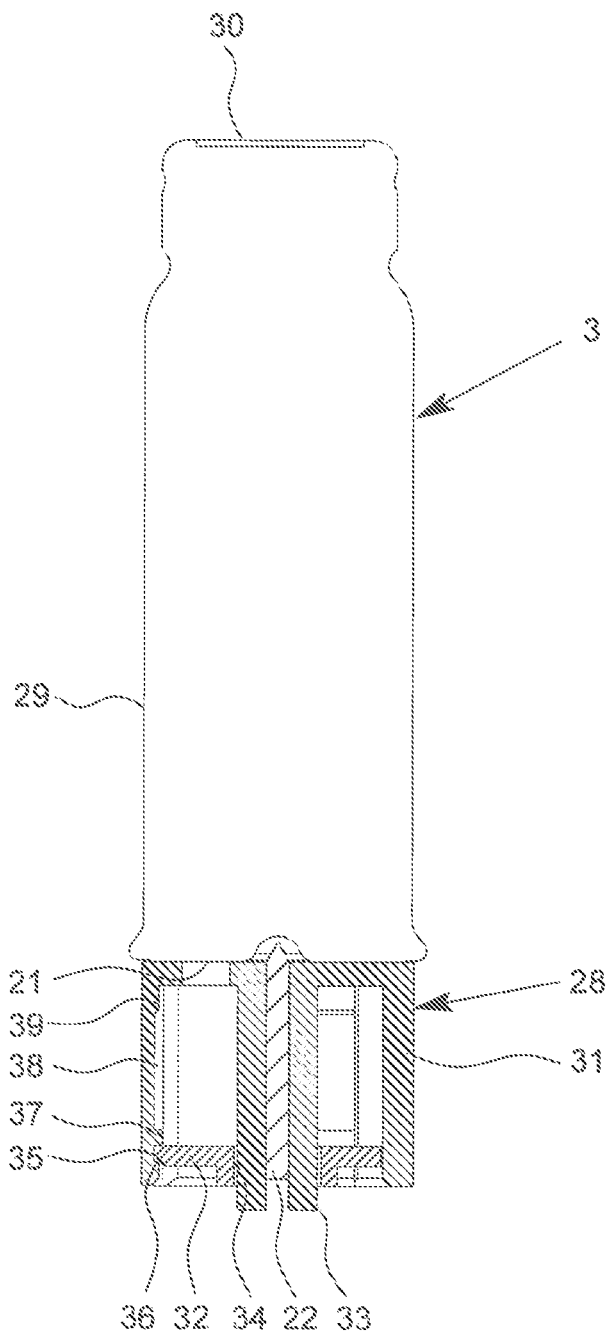
Figure 4:
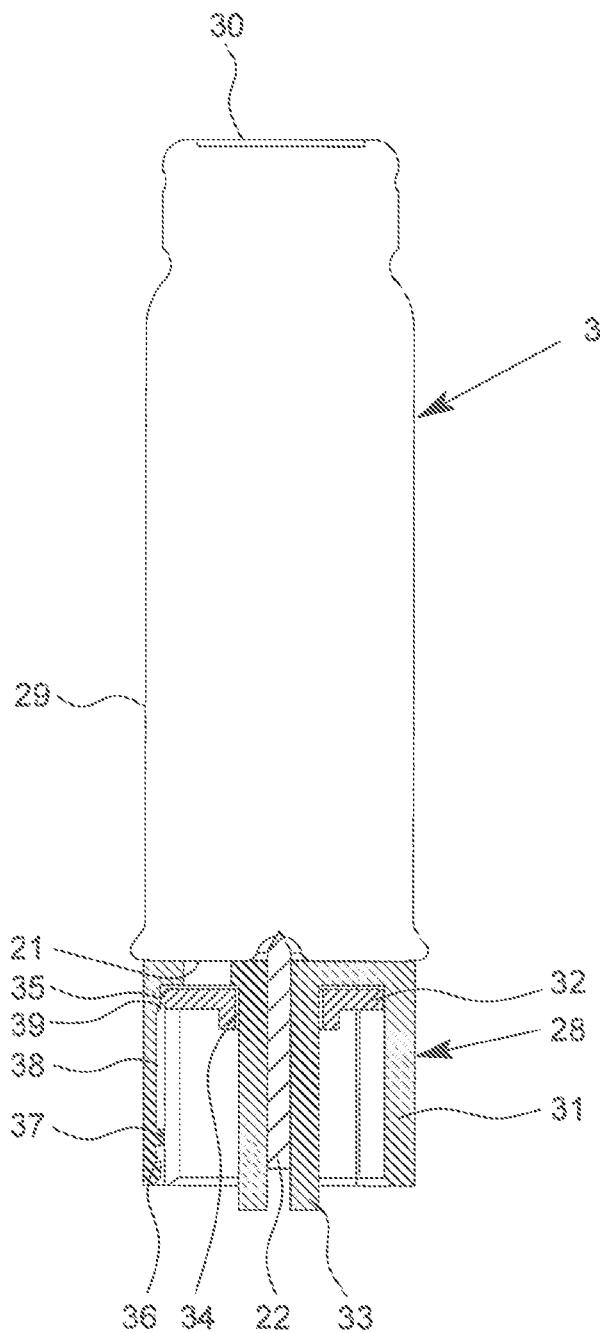
Figure 5:
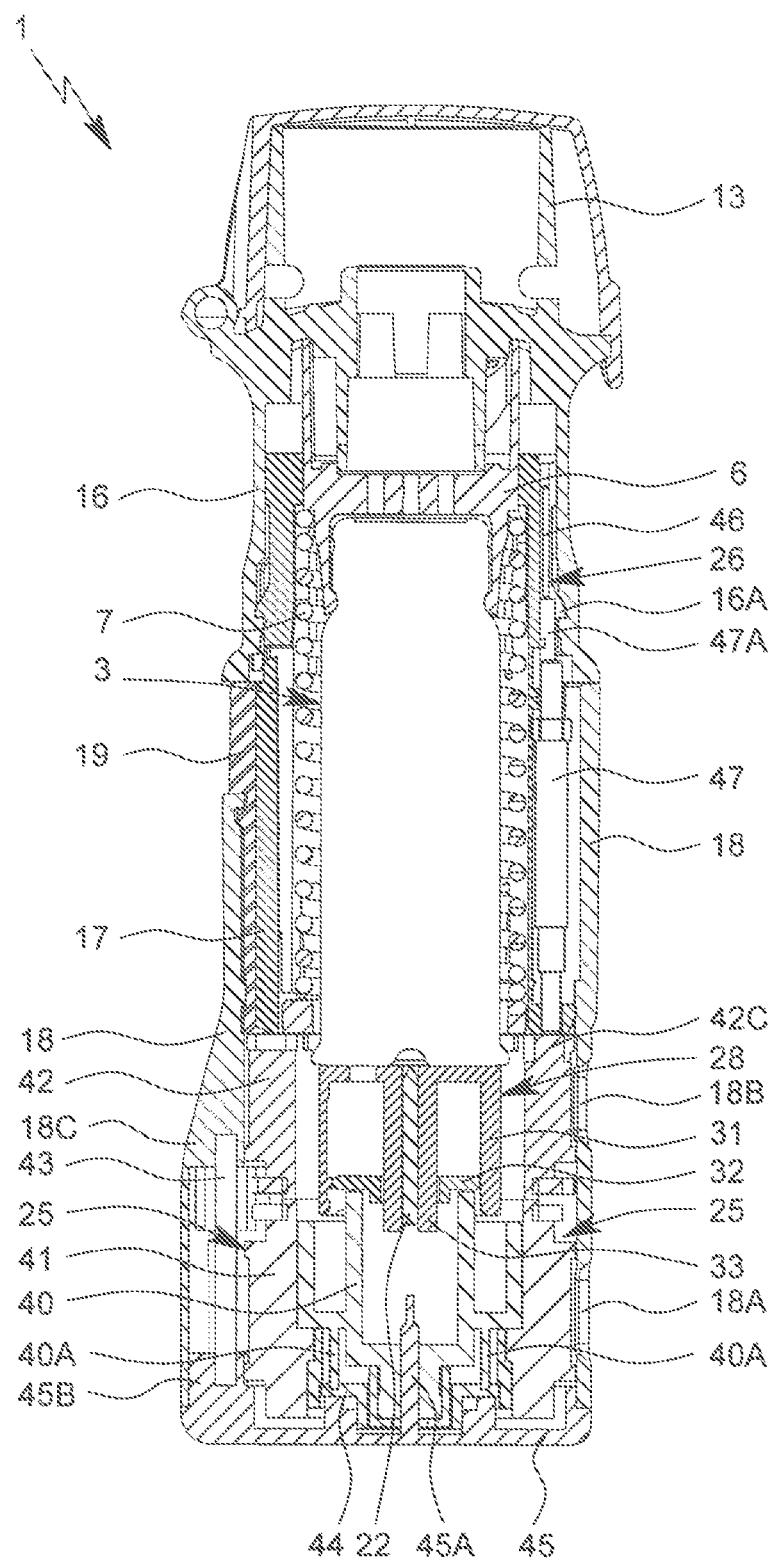
Figure 6:
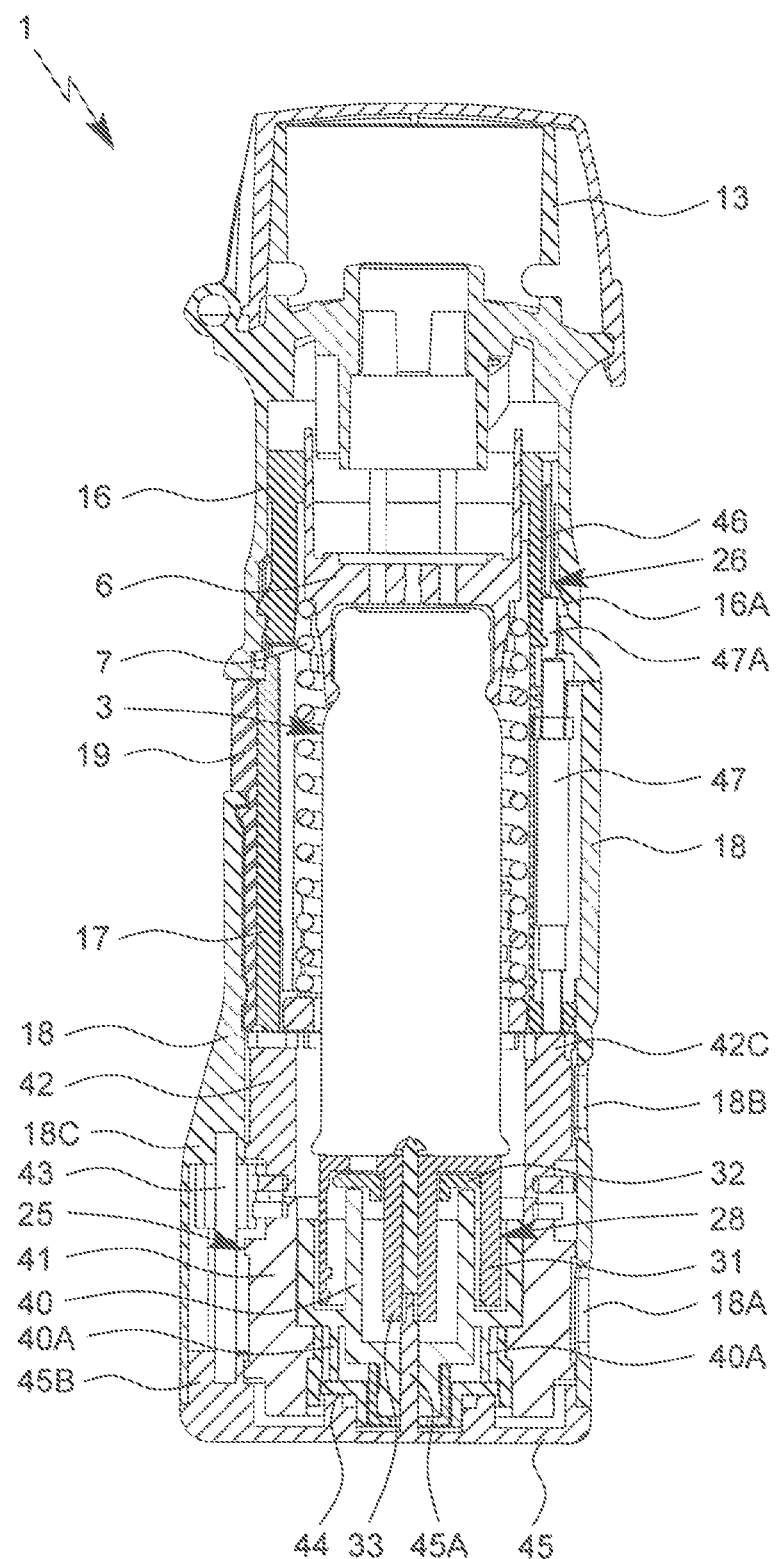
Figure 7:
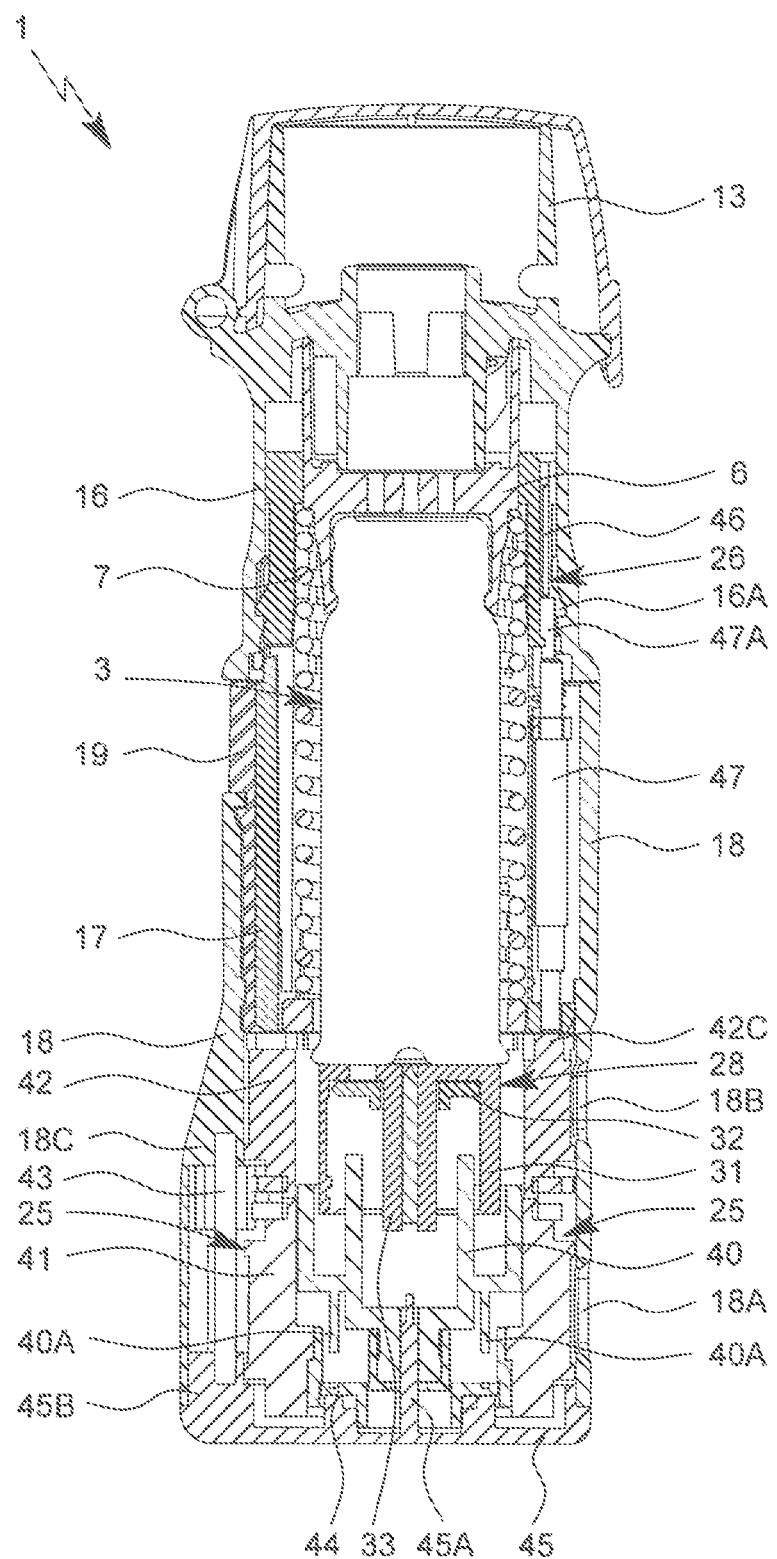
Figure 8:
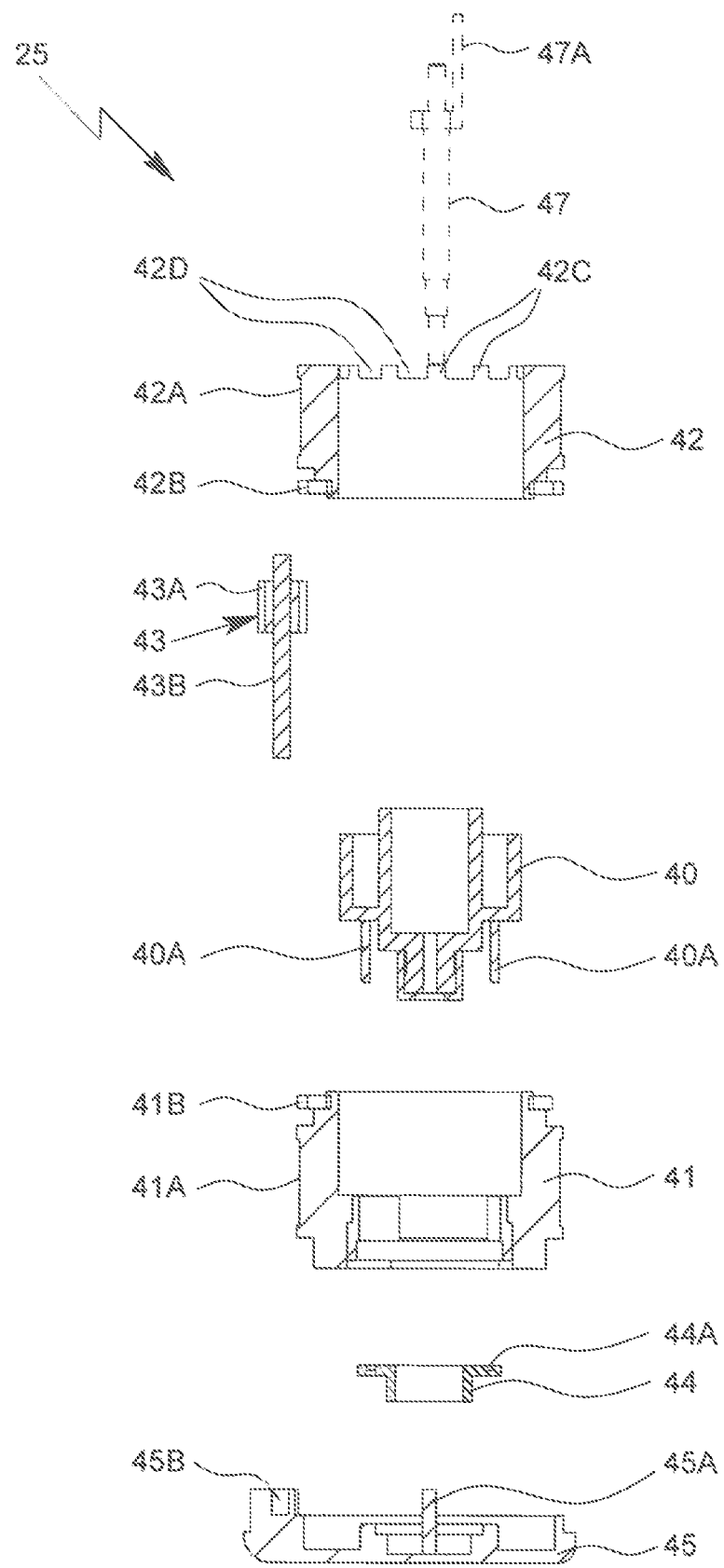

Further advantages, features, characteristics and aspects of the present invention will become apparent from the claims and the following description of a preferred embodiment with reference to the drawings. It shows:

FIG. 1 a schematic section of a known nebulizer in a non-tensioned state;

FIG. 2 a schematic section, rotated 90° compared with FIG. 1, of the known nebulizer in a tensioned state;

FIG. 3 a schematic partial section of a container with an associated control device according to a preferred embodiment of the present invention in an unused state;

FIG. 4 a schematic partial section of the container with the control device similar to FIG. 3, but in a used state;

FIG. 5 a schematic section of a nebulizer with an inserted container in a non-tensioned state according to a preferred embodiment of the present invention before first tensioning or use;

FIG. 6 a schematic section of the nebulizer with inserted container similar to FIG. 5, but in a tensioned state;

FIG. 7 a schematic section of the nebulizer with inserted container similar to FIG. 5 in a non-tensioned state, but with already used container; and FIG. 8 a schematic exploded view of an indicator device of the nebulizer.

In the Figures, the same reference numerals are used for identical or similar parts, resulting preferably in corresponding or comparable properties and advantages, even if the associated description is not repeated.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e. to allow up to 200 sprays or applications. A typical container 3, as disclosed in WO 96/06011 A1, holds e.g. a volume of about 2 to 20 ml.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the total number of uses of the nebulizer 1 and thus the number of containers 3, which can be used with the same nebulizer 1, is preferably restricted, e.g. to a total number of four, five or six containers 3. WO 2012/162305 A1 discloses additionally such a restriction to the total numbers of containers 3 which can be used with the same nebulizer 1.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3. In particular, the container 3 comprises a venting opening or hole 23 which is opened before or during first use.

The nebulizer 1 comprises a delivery mechanism, preferably a pressure generator 5, for conveying and nebulizing the fluid 2, particularly in a preset and optionally in an adjustable dosage amount.

The nebulizer 1 or pressure generator 5 comprises preferably a holder 6 for releasably holding the container 3, a drive spring 7 associated to the holder 6, only partly shown, and/or a blocking element 8 preferably in form of or with a button for preferably manual actuation or depressing. The blocking element 8 can catch and block the holder 6 and can be manually operated to release the holder 6 allowing drive spring 7 to expand.

The nebulizer 1 or pressure generator 5 comprises preferably a conveying element, such as a conveying tube 9, a non-return valve 10, a pressure chamber 11 and/or an nozzle 12 for nebulizing the fluid 2 into a mouthpiece 13.

The completely inserted container 3 is fixed or held in the nebulizer 1 via the holder 6 such that the conveying element fluidically connects the container 3 to the nebulizer 1 or pressure generator 5. Preferably, the conveying tube 9 penetrates into the container 3.

The nebulizer 1 or holder 6 is preferably constructed so that the container 3 can be exchanged.

When the drive spring 7 is axially tensioned in the tensioning process, the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the tensioned state.

During the subsequent relaxation in the nebulization process after actuation or pressing of the blocking element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1, and, thus, dispensed.

Generally, the nebulizer 1 operates with a spring pressure of 5 to 200 MPa, preferably 10 to 100 MPa on the fluid 2, and/or with a volume of fluid 2 delivered per stroke of 10 to 50 μl, preferably 10 to 20 μl, most preferably about 15 μl. The fluid 2 is converted into or nebulized as aerosol 14, the droplets of which have an aerodynamic diameter of up to 20 μm, preferably 3 to 10 μm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

The nebulizer 1 comprises preferably a housing 24 and/or (upper) housing part 16 and optionally a biasing or inner part 17 preferably which is rotatable relative thereto (FIG. 2) and/or has an upper part 17*a* and a lower part 17*b* (FIG. 1).

The nebulizer 1 or housing 24 comprises preferably a (lower) housing part 18. This part 18 is in particular manually operable, and/or releasable fixed, particularly fitted or held onto the inner part 17, preferably by means of a retaining element 19.

Preferably, the housing parts 16 and 18 and/or other parts form the housing 24 of the nebulizer 1.

In order to insert and/or replace the container 3, preferably the housing 24 can be opened and/or the housing part 18 can be detached from the nebulizer 1, inner part 17 or housing 24.

Generally and preferably, the container 3 can be inserted before the housing 24 is closed and/or before the housing part 18 is connected to the housing 24. The container 3 may be inserted, opened and/or fluidically connected to the delivery mechanism automatically or simultaneously when (completely) connecting the housing part 18 to the housing 24/nebulizer 1 and/or when (completely) closing the housing 24/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation of an actuation member, here preferably by rotating housing part 18 or any other component.

The actuation member, preferably the housing part 18, can be actuated, here rotated relative to the upper housing part 16, carrying with it or driving the inner part 17. The inner part 17 acts on a gear or transmission to transform the rotation in an axial movement. As a result the drive spring 7 is tensioned in the axial direction by means of the gear or transmission (not shown) formed between the inner part 17, in particular its upper part 17*a*, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus the container 3 executes a lifting or stroke movement during the tensioning process and during the nebulizing process.

The housing part 18 preferably forms a cap-like lower housing part and/or fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal or foil 50 thereon with a piercing element 22 when the container 3 makes contact with it for the first time, to allow air in or aeration, preferably by opening or piercing venting hole 23. The venting hole 23 allows for pressure compensation inside the container 3 when fluid 2 is drawn from the container 3 during the actuation of the nebulizer 1.

The nebulizer 1 comprises preferably an indicator device 25 and/or a locking device 26, as shown in FIG. 1.

The indicator device 25 indicates or counts in particular actuations of the nebulizer 1, preferably by detecting its tensioning or the rotation of the inner part 17 relative to the upper part 16 or housing 24.

Preferably, the indicator device 25 or associated locking device 26 blocks the nebulizer 1 against (further) actuation or use, e.g. blocks further rotation of the housing part 18/inner part 17 and, thus, tensioning of the nebulizer 1 or its drive spring 7 and/or blocks actuation of the blocking element 8, in a locked state when a certain or predetermined number of uses, actuations and operations or discharged doses has been reached or exceeded.

Preferably, the locking device 26 comprises a locking element 27, such as a spring, in particular a leaf spring, or the like, and/or is integrated into the upper housing part 16 of the nebulizer 1.

The nebulizer 1 has preferably a longitudinal form or axis which corresponds to the axial direction and/or to the main dispensing direction and/or to stroke movement of the container 3 during tensioning and dispensing.

In the following and with reference to the further figures, a preferred embodiment of the nebulizer 1 and container 3 is described and shown according to the invention, wherein primarily important aspects and differences will be described and the previous aspects, features and explanations apply preferably additionally or correspondingly even without repetition.

FIG. 3 shows the container 3 together with an associated control device 28 according to the present invention in a schematic, partial section (longitudinal section) in a first, unused state. FIG. 4 shows the container 3 with its control device 28 in a similar section, but in a second, used state.

Preferably, the control device 28 is directly and/or unreleasably secured or fixed to or connected with the container 3. In particular, the control device 28 is associated to a respective container 3. If the container 3 of the nebulizer 1 is replaced, the control device 28 is necessarily or positively replaced as well.

In the present embodiment, the control device 28 is preferably directly connected to or abuts at an outer, preferably cylindrical case or preferably rigid housing 29 of the container 3.

Preferably, the control device 28 is fixedly arranged at the preferably flat bottom or container base 21 of the container 3 and/or opposite to an outlet or head 30 of the container 3.

It has to be noted that different constructional solutions are possible for connecting the container 3 or its housing 29 with the control device 28 or its housing 31 or vice versa. In particular, the two parts can be connected with each other by welding, brazing, gluing, screwing, clamping, hot-pressing, or the like.

Alternatively or additionally, the control device 28 and the container 3 may be connected by form-fit and/or snap-fit with each other. For example, the control device 28 can grip around a transversal protrusion or wider base 21 of the container 3 to realize a form-fit connection therewith.

The diameter of the control device 28 is preferably at least essentially equal to or slightly greater than the diameter of the container 3 or its edge.

The control device 28 comprises a housing 31 and/or preferably has an at least essentially cylindrical form.

The control device 28 or its housing 31 is preferably attached to the container 3 or its base 21 or housing 29 with an at least essentially flat and/or axial side.

The control device 28 or its housing 31 comprises a preferably control member 32 for indicating the use state of the associated container 3.

The control device 28 or control member 32 indicates initially an unused state of the associated container 3 in particular by the position of the control member 32.

Preferably, the control member 32 is initially in a first or non-actuated or non-depressed position.

Preferably, the control member 32 is in another or second position or has left the first position when or after the associated container 3 is used with the nebulizer 1 for the first time or is inserted in the nebulizer 1 for the first time and/or when or after the nebulizer 1 or its housing part 18 has been closed (completely) for the first time with the associated container 3 and the control device 28 being inside.

FIG. 3 shows the control member 32 in the first position. FIG. 4 shows the control member 32 in the second position.

In particular, the second position is achieved or reached during the first tensioning of the nebulizer 1 with the container 3 and/or during (the first) axial movement of the container 3 within the nebulizer 1 or relative thereto.

Preferably, the second position is closer to the container 3 than the first position.

Preferably, the control device 28 moves towards the container 3 or its base 21 when moving from the first position to the second position.

Preferably, the control device 28 can not be reset. In particular, the control member 32 can not be moved back into the first position.

Preferably, the control member 32 is moveable only within the control device 28 or its housing 31.

Preferably, the control member 32 is moveable axially and/or depressable.

Preferably, the control member 32 is moveable only once from the first position into the second position.

Preferably, the control member 32 is held or received within the housing 31.

Preferably, the control member 32 is dish-like or ring-like and/or is at least substantially flat.

The control device 28 or housing 31 comprises preferably a central bolt or portion 33 which extends preferably axially and/or through an opening 34 of control member 32 and/or extends at least essentially up to the free end of the control device 28 (in the first position or always) or housing 31 and/or protrudes over the control member 28 in order to secure the control member 28 against actuation or depression by inappropriate use.

Preferably the central portion 33 forms an axial guidance for the control member 32 and/or prevents tilting of the control member 32, in particular due to a preferred tube-like or sleeve-like extension of the opening 34 in axial direction around portion 33. However, other constructional solutions are possible for realizing an axial guidance.

Preferably, the control member 32 is held by a form-fit, force-fit or snap-fit in the first and/or second position.

In the present embodiment, the control member 32 is held preferably by form-fit or snap-fit in the first position and/or preferably by force-fit in the second position.

Preferably, the control member 32 engages with at least one engagement portion 35 into a respective recess 36 of the control device 28 or housing 31 in the first position, as indicated in FIG. 3.

In the preferred embodiment, the control member 32 comprises one or more engagement portions 35 circumferentially distributed for engaging into a preferably ring-like grove or recess 36 or multiple associated recesses 36. However, other constructional solutions are possible as well.

Preferably, the control device 28 or housing 31 comprises at least one shoulder 37 adjacent to or bordering the recess 36 to hold or secure the control member 32 in the first position.

Preferably, the control device 28 or control member 32 is constructed such that a predetermined control force has to be applied to axially move or depress the control member 32 to leave the first position. The cooperation of the engagement portion 35 with the respective shoulder 37 is one possible and preferred solution in order to achieve the desired control force. This control force is used for resetting, actuating or controlling, in particular unlocking the locking device 26, in particular via the indicator device 25, as explained later with reference to the further FIGS. in detail.

Preferably, the control device 28 or its housing 31 comprises a radial recess or axial extending slit 38 associated to each engagement portion 35 so that the control member 32 can move easily in axial direction from the first position towards the second position after passing the shoulder(s) 37.

In the second or axially depressed or actuated position shown in FIG. 4, the control member 32 is held preferably by form-fit or press-fit, in particular by radial clamping. This can be achieved for example by a respective contact of the engagement portion(s) with a sidewall or nose 39 of the control device 28 or housing 31. However, other constructional solutions are possible as well.

Preferably, the engagement portion 36 comprises a tip or tapered portion or elastic portion for facilitating deformation and/or passing the shoulder(s) 37.

Optionally, the piercing element 22 can be integrated into the control device 28 or housing 31 or central portion 33, e.g.

in the form of an axially moveable or depressable bolt or the like, as schematically indicated in FIGS. 3 and 4. However, other constructional solutions are possible as well.

The piercing element 22 opens or pierces the container 3 or a base seal or foil 50 thereon and/or the venting hole 23 when using the container 3 for the first time in the nebulizer 1, in particular during or at the end of the first tensioning stroke.

In particular, the movement of the container 3 relative to the nebulizer 1, its housing part 18, or a guiding portion 45a formed of a bottom 45 of the housing part 18 abuts/or actuates the piercing element 22 in the shown embodiment. However, other constructional solutions are possible as well.

FIG. 5 shows in a schematic section a nebulizer 1 according to a preferred embodiment of the present invention with inserted container 2 including the control device 28 according to the present invention.

The nebulizer 1 comprises preferably the indicator device 25. Preferably, the indicator device 25 is located or arranged within the (lower) housing part 18.

FIG. 5 shows non-tensioned state or delivery state of the nebulizer 1 with freshly inserted container 3. With other words, the container 3 has been inserted for the first time, but not yet used in the sense of withdrawal of any fluid 2. This means that the nebulizer 1 has not been tensioned with the shown container 3 and control device 28. The control member 32 has just left the first position.

FIG. 6 shows the nebulizer 1 in a similar schematic section as FIG. 5, but in the tensioned state, i.e. prepared for fluid delivery or firing. The control member 32 is (pushed) in the second position.

FIG. 7 shows the nebulizer 1 in a schematic section similar to FIG. 5 and also in a non-tensioned state, but after tensioning of the nebulizer 1 and fluid delivery, i.e. with the control member 32 in the second position.

FIG. 8 shows in a schematic exploded view the indicator device 25 according to the preferred embodiment, i.e. essential components of the indicator device 25.

In the present embodiment, the indicator device 25 comprises preferably an actuation element 40, a first indicator element 41, a second indicator element 42, a coupling or coupling element 43 to coordinate movement or indexing of the indicator elements 41 and 42, a drive element 44 and/or a base 45.

Preferably, the indicator device 25 or first indicator element 41 indicates or counts and/or displays the number of uses still possible or already performed with the current container 3. In particular, the first indicator element 41 shows respective numbers, markings, symbols or the like, preferably on its outside or circumferential wall 41A.

The current number of uses is indicated or shown or can be seen preferably through an associated window 18A in the nebulizer housing 24 or housing part 18. However, other constructional solutions are possible as well.

The first indicator element 41 is preferably sleeve-like and/or hollow.

Preferably, the first indicator element 41 is rotatable about the longitudinal axis or stroke axis of the nebulizer 1 and/or container 3.

Preferably, the actuation element 40 drives, actuates or indexes the indicator device 25 or first indicator element 41. In particular, the actuation element 40 transforms the axial or stroke movement of the container 3 and control device 28 into the desired rotational (stepwise) movement.

The actuation element 40 is preferably axially moveable with respect to the longitudinal axis or stroke axis of the nebulizer 1 or container 3 and/or control device 28.

Preferably, the actuation element 40 is essentially cylindrical or sleeve-like.

In the shown embodiment, the actuation element 40 comprises preferably an outer, preferably ring- or sleeve-like portion for outer and/or axial guiding the actuation element within the first and/or second indicator element 41, 42.

In particular, the actuation element 40 comprises an inner protruding and/or sleeve-like actuation portion for abutting and/or actuating or cooperating with the control device 28 or control member 32.

Preferably, an annular or ring-like space is formed between the outer portion and inner portion of the actuation element 40 so that the preferably sleeve-like housing 31 of the control device 28 can protrude or move into this space when the container 3 and the control device 28 move into the lower position (tensioned position of the nebulizer 1) or when the container 3 is approaching the indicator device 25, as shown in FIG. 6.

Preferably, the actuation element 40 or its inner portion is hollow so that the central portion 33 of the control device 28 can move into the actuation element 40 or its inner portion when the container 3 and the control device 28 move into the lower position (tensioned position of the nebulizer 1) or when the container 3 is approaching the indicator device 25, as shown in FIG. 6.

The actuation element 40 is preferably arranged within and/or coaxially with the first and/or second indicator element 41, 42.

In the shown embodiment, the actuation element 40 comprises or holds at least one, here two actuation arms 40A extending in particular axially and being flexible and inclined in circumferential direction. The at least one actuation arm 40A is biased in axial direction (stroke axis), here against the drive element 44, so that the actuation element is pushed upwards in the drawings and/or towards the container 3 or control device 28 when inserted into the nebulizer 1.

The at least one actuation arm 40A cooperates with the drive element 44, in particular with preferably inclined and/or asymmetrical depression or teeth 44A (schematically shown in FIG. 8) on the axial or end face of the drive element 44, so that a downward movement of the actuating element 40 from the upper position shown in FIG. 7 to the lower position shown in FIGS. 5 and 6 results in that the at least one actuation arm 40A is stressed to bend and thereby rotate or index the drive element 44 in the desired rotational direction.

The drive element 44 is rotatably coupled with the first indicator element 41 and can rotate preferably coaxially. In particular, the drive element 44 is arranged at or at least partially within the first indicator element 41 and/or forms a (lower) rotational bearing for the first indicator element 41 on the axial end or base 45 forming the lower end of the housing part 18.

However, other constructional solutions are possible as well. For example, the actuation element 40 can also cooperate or drive the indicator device 25 or its first indicator element 41 by engaging into inclined or asymmetrical teeth or coves or the like formed at the inner circumferential wall of the indicator element 41 or any other component.

A ratchet mechanism (not shown) can be provided to prevent that the drive element 44 and/or first indicator element 41 can rotate in opposite direction, in particular when the actuating element 40 is moved back into its upper position during fluid delivery or firing, and/or can freely rotate.

The nebulizer 1 comprises the housing part 18 which can be opened or detached for inserting or replacing the container 3.

Preferably, the housing part 18 is cap-like and/or closed at its lower end by base 45. In particular, the base 45 is inseparably connected to the housing part 18.

The actuation element 40 is preferably guided in the housing part 18 or indicator device such that it can axially move between its upper and lower positions, but is held non-rotatably. The non-rotatable guidance can be achieved for example by means and guiding portion 45A protruding axially from the base 45 with a non-rotational cross-section engaging into a corresponding opening of the actuation element 40. However, other constructional solutions are possible in order to achieve the desired axial movability and non-rotational guidance of the actuation element 40, for example by one or more axially extending ribs and groves which cooperate or engage.

Preferably, the indicator device 25 or second indicator element 42 indicates or counts and/or displays the number of containers 3 which can still be used or which have already been used with the nebulizer 1. In particular, the second indicator element 42 shows respective numbers, markings, symbols or the like, preferably on its outside or circumferential wall 42A.

Additionally or alternatively, the indicator device 25 or its first or second indicator element 41 or 42 can indicate when the locked state is reached and/or the container 3 has to be replaced, in particular by showing a respective symbol, such as a cross or arrow or the like.

The current number, marking, symbol or the like of the second indicator element 42 can be seen preferably through an associated window 18B in the nebulizer housing 24 or housing part 18. However, other constructional solutions are possible as well.

The second indicator element 42 is preferably sleeve-like and/or hollow.

Preferably, the second indicator element 42 is rotatable about the longitudinal axis or stroke axis of the nebulizer 1 and/or container 3 and/or is rotatable coaxially to the first indicator element 42.

Preferably, the first and second indicator elements 41 and 42 are axially arranged one adjacent to the other.

The rotation or indexing of the first and second indicator elements 41, 42 is preferably coupled, in particular by a suitable transmission, in the preferred embodiment by means of the coupling element 43.

In the shown embodiment, the coupling element 43 comprises a gear 43A which is rotatably held in particular by an axle 43B or the like.

Preferably, the coupling element 43 or axle 43B is rotatably held by a bearing portion 45B formed at or by the base 45 and/or by a bearing portion 18C formed by housing part 18. However, other constructional solutions are possible as well.

Preferably, a ratchet mechanism (not shown) can be provided to prevent free and/or backwards rotation of the coupling element 43 and/or second indicator element 42.

The first indicator element 41 comprises preferably an outer toothing 41B which extends only partially around the circumference of the first indicator element 41 and can mesh with the coupling element 43 or gear 43A.

The second indicator element 42 comprises preferably an outer toothing 42B which preferably meshes always with the coupling element 43 or its gear 43A.

Thus, a coupling or transmission can be achieved such that the second indicator element 42 is indexed one step further (only) when the predetermined number of uses has been reached or exceeded in order to enter or initiate the locked state.

The coupling or transmission, in particular the circumferential length of the partial toothing 41B, is made in particular such that the next rotational or indexing step of the first indicator element 41 is also transmitted via the coupling element 43 to the second indicator element 42 in order to reset or release the locked state. This required actuation or indexing of the indicator device 25 or first indicator element 41 is called "reset actuation" hereinafter.

Alternatively or additionally, the term "reset actuation" refers to the first actuation of the indicator device 25 and/or the actuation to unlock the locking device 26 and/or to unblock the nebulizer 1, when an unused container 3 is connected to or inserted into the nebulizer 1 for the first time, in particular when completely closing the nebulizer 1 with the unused container 3 being inside.

Preferably, the nebulizer 1 is delivered in the locked state, i.e. with the locking device 26 blocking use of the nebulizer 1, in particular blocking any tensioning of the nebulizer 1. With other words, the nebulizer 1 is blocked against use in the delivery state, i.e. without connected or inserted container 3.

The reset actuation results preferably in that the first indicator element 41 starts again with indicating or counting the number of uses and/or in that the indicator device 25 or first indicator element 41 is reset.

In the locked state, the nebulizer 1 is blocked against further use by means of the locking device 26. In particular, the locking device 26 blocks any further tensioning, preferably any further rotation of the inner part 17 relative to the upper part 16, in the locked state. Preferably, the nebulizer 1 is delivered in such a state without inserted container 3. Further, the nebulizer 1 assumes the same locked state if the container 3 has been used and must be replaced by an unused or fresh one.

When the unused container 3 is initially inserted, the control device 28 or its control member 32 is in the first position indicating the unused state.

When closing the nebulizer 1 or its housing 24 or housing part 18, the control device 28 or control member 32 initiates or leads to the reset actuation before reaching the completely closed state.

In particular, the control member 32 is initially in the first position and the actuation element 40 abuts against the control member 32 early before the nebulizer 1 or housing part 18 is completely closed. During the further closing movement (in particular, the housing part 18 is pushed onto the inner part 17) the actuation element 40 is moved axially and/or relatively within the housing part 18 and/or indicator device 25 and/or performs the reset actuation, namely indexes the first indicator element 41 by one step (rotational increment) which, in turn, indexes via the coupling (here, the partial toothing 41B, coupling element 43 and toothing 42B) the second indicator element 42 by one step (rotational increment) as well.

In order to ensure a secure reset (actuation) the control force which holds the control member 32 in its first position, has to be set sufficiently high, in particular higher than the force for actuating or resetting the indicator device 25 and/or for unlocking the locking device 26 which forms a first threshold. Thus, the control force has to be higher than the first threshold.

During the closing movement, the actuating element 40 reaches its lower (end) position before completely closing the nebulizer 1. Thus, the final further closing movement pushes the control member 32 out of its first position and/or over shoulder(s) 37 into an intermediate position when the nebulizer 1 is finally completely closed as schematically shown in FIG. 5. Thus, the control force holding the control member 28 in the first position is overcome during the final closing movement. Therefore, the force which acts between the lower housing part 18 or the indicator device 25 on one hand and the container 3 or the control device 28 on the other hand when approaching the final closing movement depends on the force applied by the user and should not be too high. This force forms a second threshold, and the control force has to be (sufficiently) lower than this second threshold.

It has to be noted that the nebulizer 1 is still in the non-tensioned state, i.e. during the initial or previous locked state and during container insertion or replacement and during closing the nebulizer 1.

The reset actuation of the indicator device 25 takes place early enough so that the indicator device 25 or its second indicator element 42 is reset or moved further from the locked state or position to the unlocked state or position.

FIG. 6 shows the nebulizer 1 in the tensioned state. During the first tensioning stroke (downward movement of container 3 and control device 28 starting from the non-tensioned state shown in FIG. 5) the actuation element 40 pushes the control member 32 from the intermediate state shown in FIG. 5 into the second position shown in FIG. 6. In particular, the control member 32 is axially moved or depressed (into the control device 28 or its housing 31 or into the second position). As already explained, the control member 32 is preferably held in the second position so that this pushing action takes place only during the first tensioning.

If the optional piercing element 22 is provided, it is possible that the piercing element 22 is automatically actuated during the first tensioning. For example, the piercing element 22 could be axially pushed into its piercing position by the axial movement of the container 3 or control device 28 relative to the housing part 18 or indicator device 25 during first use or tensioning, preferably by the guide portion 45A as schematically shown in FIG. 6. However, other constructional solutions are possible as well.

FIG. 7 shows the nebulizer 1 in the non-tensioned state after first or multiple use(s). It is visible that the control device 28 or control member 32 remains in the second position indicating the used state.

As already mentioned, the locking device 26 is preferably controlled or actuated by the indicator device 25 and/or control device 28, preferably by the control device 28 via the indicator device 25. Thus, the indicator device 25 preferably controls or actuates the locking device 26 in the shown and preferred embodiment. However, the control device 28 could also control or actuate the locking device 26 directly or via an additional actuation element or the like.

The locking device 26 is preferably arranged at the inner part 17.

The locking device 26 comprises preferably a control element 47 for controlling the locking element 46.

Preferably, the locking element 46 is formed by a spring which is biased in axial direction from a non-locking position shown in FIGS. 5 to 7 downwards into a locking position.

The locking element 46 or spring is preferably constructed such that it expands or engages automatically into a counter recess, preferably a pocket 16A formed in the upper housing part 16, to block further tensioning of the nebulizer 1 in the locked state.

It has to be noted that the locking element 46 is axially moveably held at the inner part 17, in particularly biased by itself or a separate spring downwards into the locked position or for blocking.

The nebulizer 1 or housing part 16 comprises preferably two engagement recesses or portions, in particular two pockets 16A, offset by 180° so that the locking device 26 or locking element 46 can block the nebulizer 1 against further use in each possible rotational end position. In this context, it has to be noted that the nebulizer 1 or its inner part 17 and housing part 18 are rotated by 180° during each tensioning.

The locking device 26 or control element 47 is constructed to keep or hold the locking element 46 in the upper or non-locking position as long as the nebulizer 1 is completely closed and/or the indicator device 25 has not entered the locked state, in particular as long as the indicator device 25 or its second indicator element 42 or a protrusion 42C thereof pushes the control element 47 and, thus, the locking element 46 in the upper or non-locking position as shown in FIGS. 5 to 7.

In FIG. 8, the cooperation of the indicator device 25 or its second indicator element 42 on one hand and the control element 47 on the other hand is indicated schematically.

In particular, the second indicator element 42 comprises at least one protrusion 42C and/or recess 42D—in particular alternatively protrusions 42C and recess 42D—preferably at its end or axial face and/or any other suitable position for cooperating with or axially actuating the locking device 26 or its control element 47.

As shown in FIG. 8, preferably, the control element 47 comprises or is connected with a control portion 47A which extends towards the locking element 46 for pushing the locking element 46 upwards into the non-locking position when the control element 47 is held or pushed in its upper position shown in FIGS. 5 to 7.

When the locked state is reached or to be entered, the indicator device 25 or its second indicator element 42 is indexed one rotational step further so that the protrusion 42C does not support the control element 47 any longer. Consequently, the control element 47 can move axially downwardly into the (next) recess 42D in particular due to the biasing force of the locking element 46 and/or any other spring. This axial movement allows the locking element 46 to move into the locked position, in particular radially preferably into a pocket 16A, so that the locking device 26 or its locking element 46 can (automatically) block the nebulizer 1 against further use or tensioning in the locked state.

As already mentioned, the locked state of the locking device 26 can be reset or released when the used container 3 is replaced against an unused container 3 and the nebulizer 1 is completely closed. In particular, the insertion of the unused container 3 (together with its control device 28 control member 32 in the first position) results in the reset actuation already explained above so that the indicator device 25 or its second indicator element 42 is indexed one step further before complete closing which results in that a protrusion 42C is moved again below the control element 47 and can push the control element 47 axially upwards when completely closing the nebulizer 1. Thus, the locking device 26 is reset or unlocked and the nebulizer 1 is unblocked.

It has to be noted that the indicator device 25 counts preferably the number of containers 3 that have been used or can still be used with the nebulizer 1. If a predetermined number of containers 3, e.g. four, five or six containers 3, is reached, the nebulizer 1 is preferably finally blocked against any further use.

The above final blocking of the nebulizer 1 can be achieved via the indicator device 25, in particular in that the final or last recess 42C is made longer in circumferential direction such that any final reset actuation of the indicator device 25 does not lead to the resetting or unlocking of the locking device 26.

In consideration of the above explanation, it has to be noted that only the container 3 together with its associated control device 28 has to be replaced after usual use. The nebulizer 1 including the housing part 18 and indicator device 25 can be reused for multiple containers 3.

It has to be noted that the nebulizer 1 can be constructed such that it can be opened only after a predetermined number of uses has been reached or exceeded with the current container 3. This locking against early opening can be controlled by the indicator device 25 as well, e.g. by locking the depression of the retaining element 19 until the predetermined number of uses has been reached or exceeded with the current container 3.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

| List of reference numerals | |
|---|---|
| 1 | nebulizer |
| 2 | fluid |
| 3 | container |
| 4 | bag |
| 5 | pressure generator |
| 6 | holder |
| 7 | drive spring |
| 8 | blocking element |
| 9 | conveying tube |
| 10 | non-return valve |
| 11 | pressure chamber |
| 12 | nozzle |
| 13 | mouthpiece |
| 14 | aerosol |
| 15 | air supply opening |
| 16 | upper housing part |
| 16A | pocket |
| 17 | inner part |
| 17A | upper part of inner part |
| 17B | lower part of inner part |
| 18 | housing part (lower part) |
| 18A | first window |
| 18B | second window |
| 18C | bearing portion |
| 19 | retaining element |
| 20 | aeration spring |
| 21 | container base |
| 22 | piercing element |
| 23 | venting hole |
| 24 | nebulizer housing |
| 25 | indicator device |
| 26 | locking device |
| 27 | locking element |
| 28 | control device |
| 29 | container housing |
| 30 | container head |
| 31 | housing (control device) |
| 32 | control member |
| 33 | central portion |
| 34 | opening |
| 35 | engagement portion |
| 36 | recess |
| 37 | shoulder |
| 38 | slit |
| 39 | nose |
| 40 | actuation element |
| 40A | actuation arm |
| 41 | first indicator element |
| 41A | wall |
| 41B | toothing |
| 42 | second indicator element |
| 42A | wall |
| 42B | toothing |
| 42C | protrusion |
| 42D | recess |
| 43 | coupling element |
| 43A | gear |
| 43B | axle |
| 44 | drive element |
| 44A | tooth |
| 45 | base |
| 45A | guiding portion |
| 45B | bearing portion |
| 46 | locking element |
| 47 | control element |
| 47A | control portion |

The invention claimed is:

1. A nebulizer (1) for dispensing individual doses of a fluid (2), comprising:
a container (3) containing the fluid (2), where the container (3) is replaceable in the nebulizer (1);
an indicator device (25) for indicating a number of the individual doses that have been removed from, or are still possible from, the container (3), and
a locking device (26) for locking of the nebulizer (1) against further use when the container (3) in a locked state after a predetermined number of the individual doses have been removed from the container (3),
wherein the container (3) comprises a control device (28) for:
(i) indicating initially an unused state of the container (3) and unlocking the nebulizer (1) by unlocking the locking device (26),
(ii) indicating a used state of the container (3) when the predetermined number of doses has been reached, to at least one of prevent unlocking of the nebulizer (1), and keep the nebulizer (1) locked when connecting the container (3) to the nebulizer (1), and (iii) resetting the indicator device (25) after the container (3) has been removed and replaced with a new container (3), and upon a first individual dose being removed from the new container (3).

2. The nebulizer according to claim 1, wherein the control device (28) controls or actuates, when moved stroke-like or in an axial direction.

3. The nebulizer according to claim 1, wherein the control device (28) at least one of controls and actuates, the indicator device (25).

4. The nebulizer according to claim 1, wherein the indicator device (25) at least one of controls and actuates the locking device (26).

5. The nebulizer according to claim 1, wherein the nebulizer (1) comprises a housing (24) and a housing part (18), which is opened relative to the housing (24) for replacing the container (3).

6. The nebulizer according to claim 1, wherein the indicator device (25) is arranged in a housing part (18) of the nebulizer (1).

7. The nebulizer according to claim 1, wherein the locking device (26) is adapted to at least one of:
(i) lock tensioning of the nebulizer (1) in the locked state, and
(ii) lock moving of the container (3) axially relative to the nebulizer (1).

8. The nebulizer according to claim 1, wherein at least one of:
(i) the nebulizer (1) is locked against use in a delivery state, and
(ii) the locking device (26) is in the locked state when the nebulizer (1) is delivered, without the container (3) within the nebulizer (1).

9. The nebulizer according to claim 1, wherein the control device (28) controls the locking device (26) indirectly via the indicator device (25).

10. The nebulizer according to claim 9, wherein the control device (28) comprises a control member (32).

11. The nebulizer according to claim 10, wherein the control member (32) is moveable.

12. The nebulizer according to claim 11, wherein the control member (32) is depressible or axially moveable.

13. The nebulizer according to claim 12, wherein the control member (32) is held by form-fit, force-fit or snap-fit in a first position before a first use or insertion of the container (3) into the nebulizer (1).

14. The nebulizer according to claim 13, wherein the control member (32) is held by form-fit, force-fit or snap-fit in a second position after the first use or insertion of the container (3) into the nebulizer (1).

15. The nebulizer according to claim 14, wherein the control device (28) is arranged opposite to a dispensing opening or head (30) of the container (3) or at a bottom or base (21) of the container (3), or is inseparably connected with the container (3).

16. The nebulizer according to claim 14, wherein the control member (32) has at least one of left the first position and moved to the second position when the nebulizer (1) is initially closed with the container (3) and the control device (28) therein.

17. The nebulizer according to claim 14, wherein the control member (32) cannot be moved back into the first position after the control member (32) has been moved into the second position.

18. The nebulizer according to claim 14, wherein the control member (32) is dish-like and at least substantially flat.

19. The nebulizer according to claim 14, wherein the control device (28) comprises a central bolt (33) which extends axially through an opening (34) of the control member (32) and protrudes over the control member (32).

20. The nebulizer according to claim 14, wherein the control member (32) is depressible within the control device (28).

21. The nebulizer according to claim 14, wherein in the first position, the control member (32) engages with at least one engagement portion (35) into a respective recess (36) of the control device (28) or a housing (31) thereof.

22. The nebulizer according to claim 14, wherein the control device (28) or control member (32) is constructed such that a predetermined control force has to be applied to axially move or depress the control member (32) to leave the first position.

23. The nebulizer according to claim 1, wherein the indicator device (25) controls and actuates the locking device (26) via a rotatable part with at least one protrusion (42C) and/or recess (42D) cooperating with a control element (47) of the locking device (26).

24. The nebulizer according to claim 23, wherein, when the protrusion (42C) is moved away from the control element (47) or the recess (42D) into contact with the control element (47), the control element (47) moves, and such movement of the control element (47) moves a bolt or locking element (46) into or out of a locked position.

25. A nebulizer (1) for dispensing individual doses of a fluid (2), comprising:
a container (3) containing the fluid (2), where the container (3) is replaceable in the nebulizer (1); and
a locking device (26) for locking of the nebulizer (1) against further use when the container (3) in a locked state after a predetermined number of the individual doses have been removed from the container (3),
wherein the container (3) comprises a control device (28) for at least one of:
(i) indicating initially an unused state of the container (3) and unlocking the nebulizer (1) by unlocking the locking device (26), and
(ii) indicating a used state of the container (3) when the predetermined number of doses has been reached, to at least one of prevent unlocking of the nebulizer (1), and keep the nebulizer (1) locked when connecting the container (3) to the nebulizer (1), and
wherein the nebulizer (1) further comprises an indicator device (25) comprising at least one indicator element (41) and an actuation element (40) for indexing the indicator element, where the actuation element (40) transforms the axial movement of the container (3) and the control device (28) into a stepwise rotational movement.

* * * * *